United States Patent
Teng et al.

(10) Patent No.: US 9,039,991 B2
(45) Date of Patent: May 26, 2015

(54) BIOSENSORS AND BIO-MEASUREMENT SYSTEMS USING THE SAME

(71) Applicant: DELBio, INC, Taoyuan Hsien (TW)

(72) Inventors: Kai-Tsung Teng, Taoyuan Hsien (TW); Chi-Jui Chiu, Taoyuan Hsien (TW)

(73) Assignee: DELBio, INC., Taoyuan (TW)

( * ) Notice: Subject to any disclaimer, the term of this patent is extended or adjusted under 35 U.S.C. 154(b) by 0 days.

(21) Appl. No.: 13/734,366

(22) Filed: Jan. 4, 2013

(65) Prior Publication Data

US 2013/0177969 A1  Jul. 11, 2013

Related U.S. Application Data

(60) Provisional application No. 61/583,765, filed on Jan. 6, 2012.

(51) Int. Cl.
*G01N 27/02* (2006.01)
*G01N 33/487* (2006.01)

(52) U.S. Cl.
CPC .......... *G01N 27/02* (2013.01); *G01N 33/48771* (2013.01)

(58) Field of Classification Search
USPC ........................................................ 422/404
See application file for complete search history.

(56) References Cited

U.S. PATENT DOCUMENTS

2007/0144918 A1* 6/2007 Hsu et al. ................... 205/775
2010/0089775 A1* 4/2010 Chen et al. ................. 205/792

* cited by examiner

*Primary Examiner* — Sam P Siefke
(74) *Attorney, Agent, or Firm* — Muncy, Geissler, Olds & Lowe, P.C.

(57) ABSTRACT

A biosensor is provided. The biosensor is used to sense a biological sample and has a code representing features of the biosensor. The biosensor includes a substrate and a conductive layer. The conductive layer is disposed on a first side of the substrate and includes a first conductive loop and a second conductive loop. The first conductive loop is formed between a first node and a second node and has a first impedance. The second conductive loop is formed between the second node and a third node and has a second impedance. The code is determined according to a comparison result between the second impedance and the first impedance.

20 Claims, 8 Drawing Sheets

BIOSENSORS AND BIO-MEASUREMENT SYSTEMS USING THE SAME

CROSS REFERENCE TO RELATED APPLICATIONS

This application claims the benefit of U.S. Provisional Application No. 61/583,765, filed on Jan. 6, 2012, the contents of which are incorporated herein by reference.

BACKGROUND OF THE INVENTION

1. Field of the Invention

The invention relates to a biosensor, and more particularly, to a biosensor with a code representing its features.

2. Description of the Related Art

Currently, most bio-sensing and/or measuring meters, take blood glucose meters here for example, provide blood glucose measurement by performing a chemical reaction with an enzyme and blood from a body part, such as a fingertip, on biochemistry strips. However, due to manufacturing process limitations, reaction features of biochemistry strips, such as enzyme reaction features, manufactured during different production batches are different. The variations of the enzyme reaction feature may affect measurement results of blood glucose. Thus, for each manufacturing batch, manufacturers have to set codes related to an enzyme reaction feature of the biochemistry strips. When users use blood glucose meters, they have to enter corresponding codes through keyboards or insert corresponding code cards with programmed codes. When reading the corresponding codes, the blood glucose meters can change or set parameters of blood glucose measurement operations according to the codes, such that results of the blood glucose measurement may not be affected by variations of the enzyme reaction feature. In practice, users may enter wrong codes, or users may insert wrong code cards or forget to insert the corresponding code cards. In such cases, errors may be induced in the blood glucose measurement. Accordingly, treatment opportunities for users may be missed, or the users may take an inappropriate amount of modification, or a user's life may be threatened.

BRIEF SUMMARY OF THE INVENTION

Thus, it is desirable to provide a biosensor for sensing a biological sample which has a code representing features of the biosensor. When the biosensor is connected to a bio-measurement device, the bio-measurement device may read the code of the biosensor automatically, which hinders obtainment of erroneous measurement results and increases convenience in usage of the bio-measurement device.

An exemplary embodiment of a biosensor is provided. The biosensor is used to sense a biological sample and has a code representing features of the biosensor. The biosensor comprises a substrate and a conductive layer. The conductive layer is disposed on a first side of the substrate and comprises a first conductive loop and a second conductive loop. The first conductive loop is formed between a first node and a second node and has a first impedance. The second conductive loop is formed between the second node and a third node and has a second impedance. The code is determined according to a comparison result between the second impedance and the first impedance.

An exemplary embodiment of a bio-measurement system is provided. The bio-measurement system is used to sense a biological sample and comprises a biosensor and a bio-measurement device. The biosensor has a code representing features of the biosensor. The biosensor comprises a substrate, a biological reaction layer, and a conductive layer. The substrate has a first side and a second side opposite to the first side. The biological reaction layer is disposed in a biological reaction area on the second side of the substrate and has a chemical reagent. The biological sample is disposed on the biological reaction area for contacting with the chemical reagent of the biological reaction layer. The conductive layer is disposed on the first side of the substrate and comprises a first conductive loop and a second conductive loop. The first conductive loop is formed between a first node and a second node and has a first impedance. The second conductive loop is formed between the second node and a third node and has a second impedance. The bio-measurement device is connected to the biosensor. The bio-measurement device obtains the first impedance and the second impedance and determines a value of the code according to a comparison result between the second impedance and the first impedance. The bio-measurement device performs a measurement operation to an analyte of the biological sample according to the value of the code.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
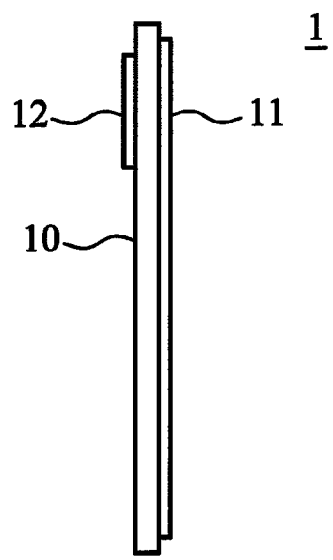
FIG. 1 shows a side view of a biosensor according to an exemplary embodiment.

Biosensors are provided. FIG. 1 shows a side view of a biosensor according to an exemplary embodiment. A biosensor 1 is used to sense at least one analyte of a biological sample. Referring to FIG. 1, the biosensor 1 comprises a substrate 10, a conductive layer 11, and a biological reaction layer 12. The conductive layer 11 is disposed on one side 10a of the substrate 10, while the biological reaction layer 12 is disposed on another side 10b of the substrate 10 which is opposite to the one side 10a.

Figure 2:
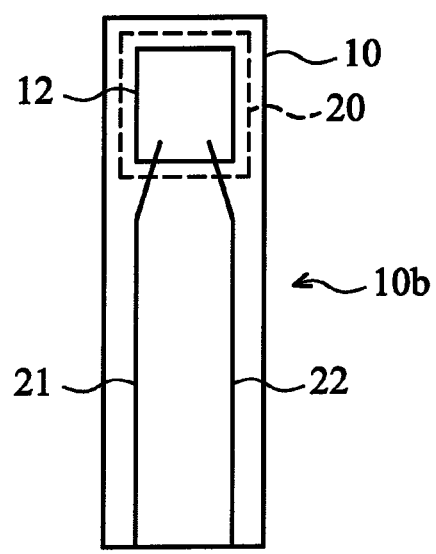
FIG. 2 shows one side of a substrate of the biosensor in FIG. 1.

FIG. 2 shows the other side 10b of the substrate 10. Referring to FIG. 2, the biological reaction layer 12 is disposed in a biological reaction area 20 on the other side 10b. The biological reaction layer 12 has a chemical reagent. When a biological sample collected from a user is dropped, absorbed, or disposed in the biological reaction area 20, a chemical action is performed with at least one analyte of the biological sample and the chemical reagent. For example, the biological sample is the blood of the user, the analyte is glucose (blood glucose) in the blood, and the chemical reagent of the biological reaction layer 12 comprises an enzyme. When the blood of the user is dropped, absorbed, or disposed in the biological reaction area 20 for contacting with the chemical reagent of the biological reaction layer 12, a chemical action is performed with the glucose in the blood and the chemical reagent (enzyme). Note that, in the embodiment of FIGS. 1 and 2, the sizes of the biological reaction layer 12 and the biological reaction area 20 are examples. In practice, the sizes of the biological reaction layer 12 and the biological reaction area 20 may be determined according to the size of the biosensor 1, the sampling amount of the biological sample, or actual requirements.

Figure 3A:
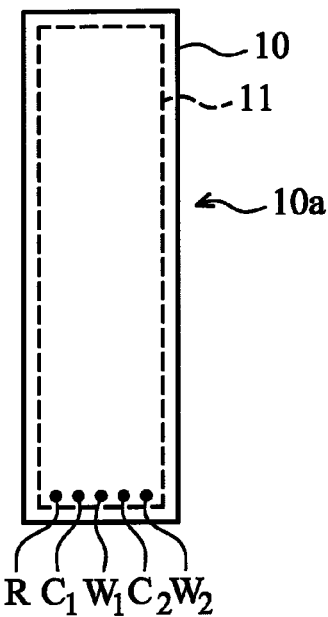
FIG. 3A show another side of a substrate of the biosensor in FIG. 1.
Figure 3B:
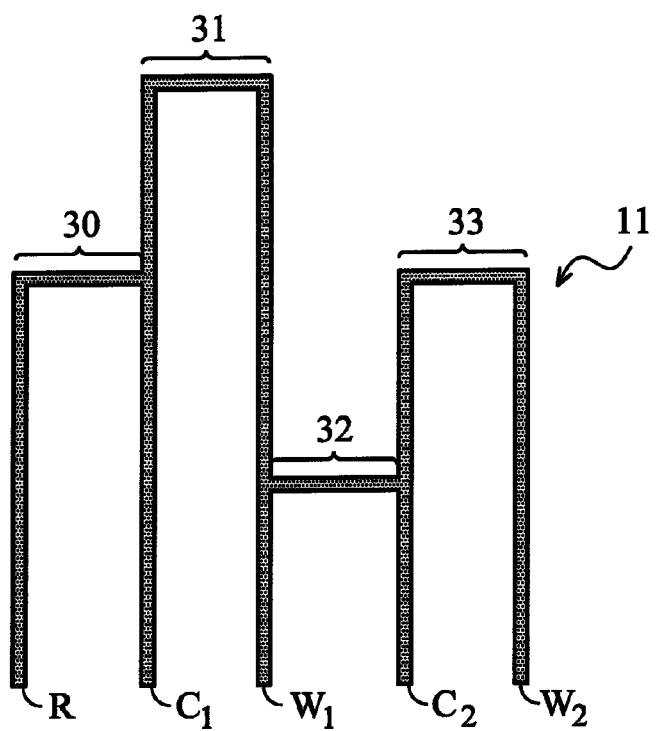
FIG. 3B shows a code pattern on the another side of the substrate of the biosensor in FIG. 3A.

FIG. 3A shows one side 10a of the substrate 10. The conductive layer 11 has a code pattern which determines a code representing manufacturing information of the biosensor 1, such as the reaction feature of the chemical reagent of the biological reaction layer 12, the date of manufacturing of the biosensor 1 (date or week number), or the correction information of the biosensor 1. The code pattern has at least two conductive loops. In the embodiment, four conductive loops are given as an example. Referring to FIG. 3A, there are five nodes R, C1, W1, C2, and W2 disposed at the lower edge of the conductive layer 11. The code pattern comprises a conductive loop formed between the nodes R and C1, a conductive loop formed between the nodes C1 and W1, a conductive loop formed between the nodes W1 and C2, and a conductive loop formed between the nodes C2 and W2. For clarity, the code pattern is shown in FIG. 3B. Referring to FIG. 3B, a conductive loop 30 is formed between the nodes R and C1, a conductive loop 31 is formed between the nodes C1 and W1, a conductive loop 32 is formed between the nodes W1 and C2, and a conductive loop 33 is formed between the nodes C2 and W2. In the embodiment of FIGS. 1 and 3A-3B, the size of the conductive layer 11 is an example. In practice, one basis for the determination of the size of the conductive layer 11 is the size of the code pattern.

In the embodiment, a value of the code is determined according to the respective impedances of the conductive loops 30~33. The impedance of each of the conductive loops 30~33 can be varied by changing the width or length of the corresponding conductive loop. For example, when the widths of the conductive loops 30~33 are substantially equal, the impedances of the conductive loops 30~33 are determined according to the lengths of the conductive loops 30~33, respectively. In the embodiment of GFIGS. 3A~3B, the impedance of the conductive loop 30 serves as a reference impedance. The impedance of the conductive loop 31 is larger than the impedance of the conductive loop 30, the impedance of the conductive loop 32 is less than the impedance of the conductive loop 30, and the impedance of the conductive loop 33 is equal to the impedance of the conductive loop 30.

In an embodiment, the conductive loops 30~33 are disposed on the substrate 10 by screen printing. When the conductive loops 30~33 are printed on the substrate 10 by paste with different materials, the conductive loops 30~33 have different impedances.

Figure 4:
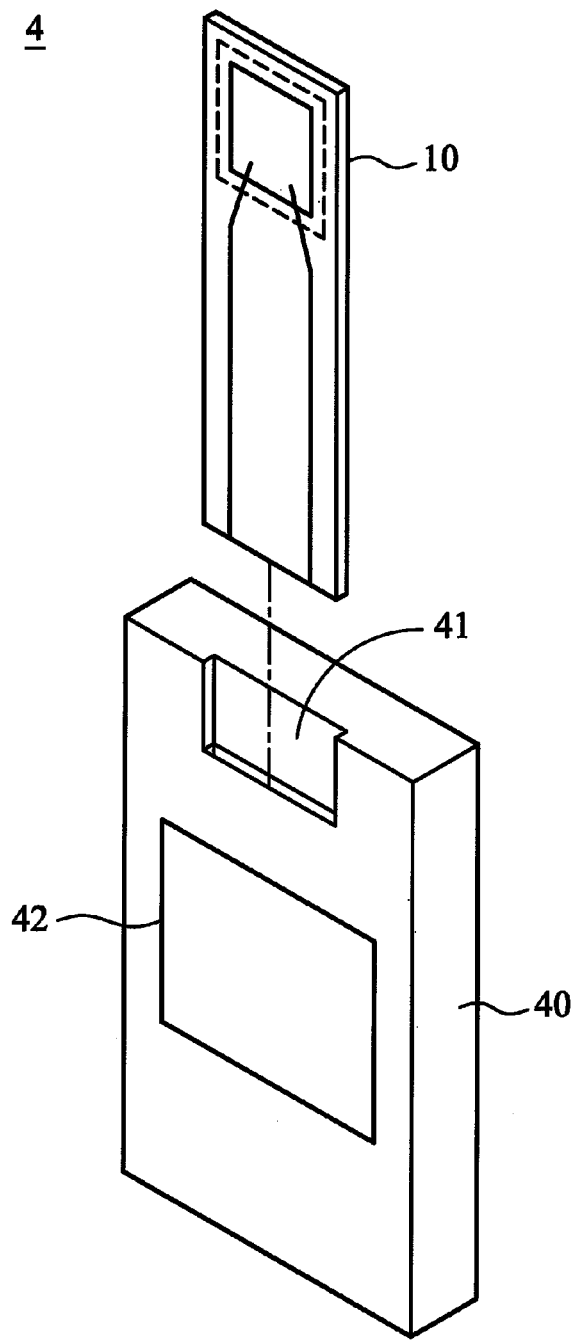
FIG. 4 shows an exemplary embodiment of a bio-measurement system.

FIG. 4 shows an exemplary embodiment of a bio-measurement system. Referring to FIG. 4, the bio-measurement system 4 comprises the biosensor 1 of FIG. 1 and a bio-measurement device 40. In an embodiment, the biosensor 1 is a blood glucose meter, and the bio-measurement system 4 is a blood glucose measurement system. In the following, a blood glucose measurement system is taken as an example to illustrate the bio-measurement system 4. When a user intends to measure or know the concentration of the glucose in the blood, the user has to insert the biosensor 1 into a slot 41 of the bio-measurement device 40 and then drop, absorb, or dispose blood in the biological reaction area 20. Referring to FIGS. 2 and 4, there are electrodes 21 and 22 disposed on the other side 10b of the substrate 10. The electrodes 21 and 22 are coupled to the biological reaction layer 12. When a chemical action is performed with the glucose in the blood and the chemical reagent (enzyme), the bio-measurement device 40 obtains electrical signals induced by the above chemical action through the electrodes 21 and 22 for a measurement operation of the concentration of the glucose in the blood.

Moreover, when the biosensor 1 is inserted into the slot 41 of the bio-measurement device 40, the bio-measurement device 40 obtains the respective impedances of the conductive loops 30~33. After the impedances of the conductive loops 30~33 are obtained, the bio-measurement device 40 determines the value of the code according to the obtained impedances. Then, the bio-measurement device 40 sets at least one parameter of the measurement operation according to the determined value of the code, such that the bio-measurement 40 can perform the measurement operation to the concentration of the glucose in the blood according to the at least one parameter. In the example of the measurement of the concentration of the glucose in the blood, the code set according to the code of the biosensor 1 is related to the reaction feature of the enzyme in the chemical reagent. Thus, when the biosensor 1 is inserted into the slot 41 of the bio-measurement device 40, the bio-measurement device 40 can read the code of the biosensor 1 automatically. Accordingly, even though the user uses several biosensors 1 manufactured by difference batches, the bio-measurement device 40 can still measures the concentration of the glucose in the blood accurately. The measurement result is not affected by different reaction features induced by different manufacturing batches, which increases measurement accuracy.

After the bio-measurement device 40 obtains the concentration of the glucose in the blood, the measurement result can be shown on a display 42 of the bio-measurement device 40, and the user or health care professional can know the concentration of the glucose in the blood from the display 42 easily.

In the following, how the bio-measurement device 40 determines the value of the code of the biosensor will be illustrated.

Figure 5:
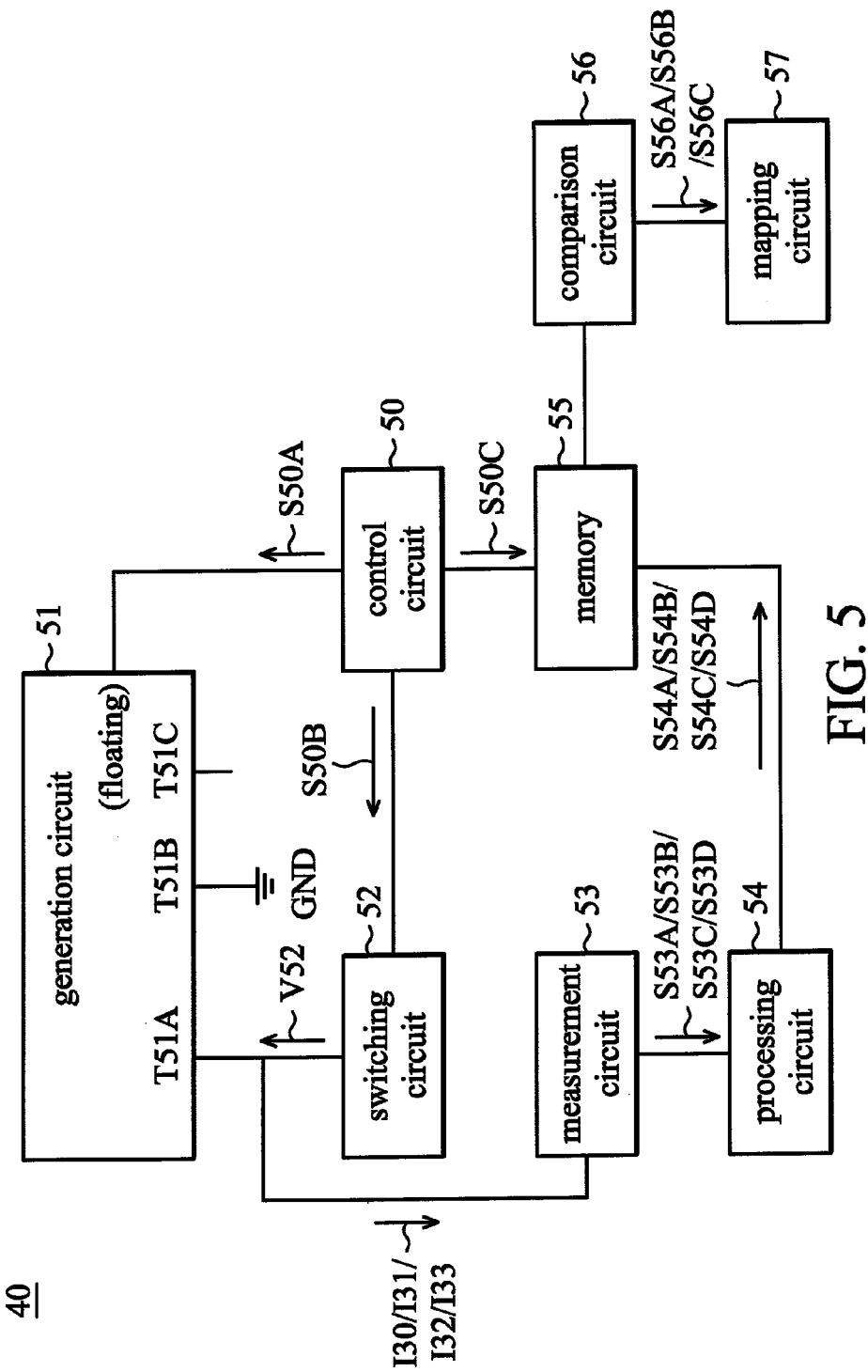
FIG. 5 shows an exemplary embodiment of a bio-measurement device of the bio-measurement system in FIG. 4.

FIG. 5 shows an exemplary embodiment of the bio-measurement device 40. Referring to FIG. 5, the bio-measurement device 40 comprises a control circuit 50, a switching circuit 51, a generation circuit 52, a measurement circuit 53, a processing circuit 54, a memory 55, a comparison circuit 56, and a mapping circuit 57. In the embodiment, the control circuit 50, the generation circuit 52, the measurement circuit 53, the processing circuit 54, the memory 55, the comparison circuit 56, and the mapping circuit 57 are included in a microcontroller unit of the bio-measurement device 40. The control circuit 50 generates control signals S50A, S50B, and S50C. The switching circuit 51 is coupled to the control circuit 50 to receive the control signal S50A. The switching circuit 51 has three input terminals T51A, T51B, and T51C. The input terminal T51B is coupled to a reference ground GND, and the input terminal T51C is at a floating state. When the biosensor 1 is inserted into the bio-measurement device 40, the switching circuit 51 couples three nodes among the nodes R, C1, W1, C2, and W2 respectively to the input terminals T51A, T51B, and T51C according to the control signal S50A. The generation circuit 52 and the measurement circuit 53 are coupled to the input terminal T51A.

Figure 6A:
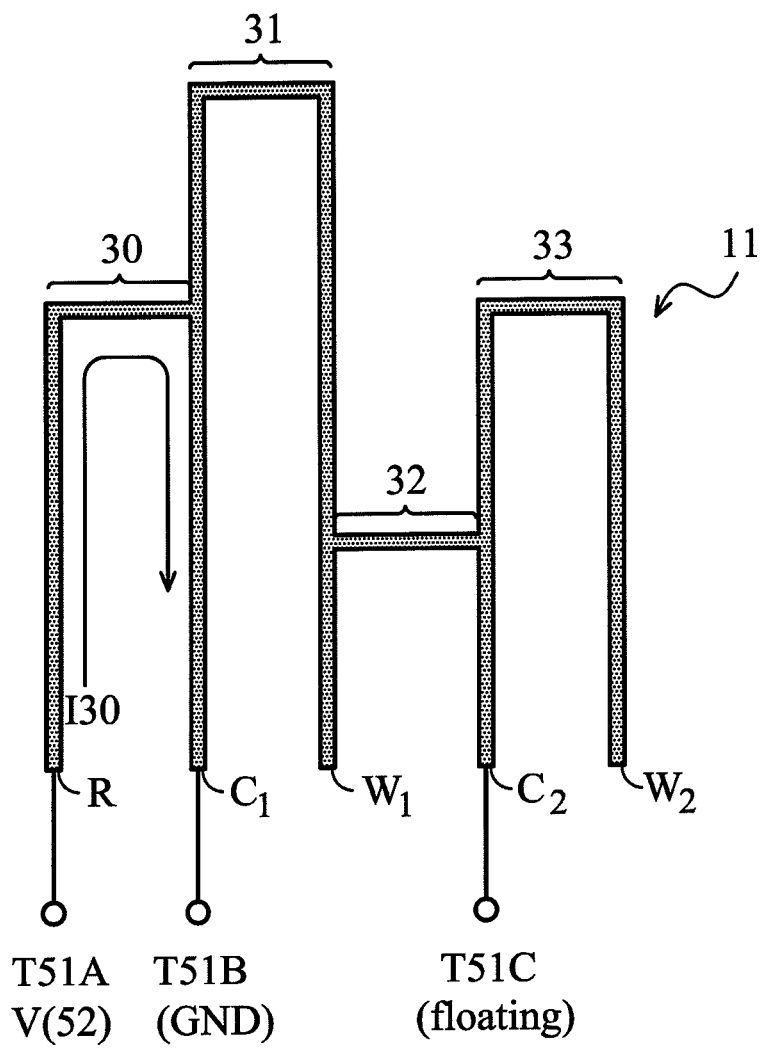
FIGS. 6A~6D are schematic views showing current measurement of conductive loops of the bio-measurement system in FIG. 4.

When the biosensor 1 is inserted into the bio-measurement device 40, the bio-measurement device 40 starts to perform the measurement operation of the concentration of the glucose in the blood. During a first measurement period, the switching circuit 51 couples the node R to the input terminal T51A, the node C1 to the input terminal (GND) T51B, and the node C2 to the input terminal (floating) T51C according to the control signal S50A, as shown in FIG. 6A. The generation circuit 52 is coupled to the control circuit 50 to receive the control signal S50B. The generation circuit 52 generates a predetermined voltage V52 to the node R through the input terminal T51A according to the controls signal S50B. At this time, a current I30 is induced from the node R to the node C1 (GND), and the amount of the current I30 is determined according to the predetermined voltage V52 and the impedance of the conductive loop 30 formed between the node R and the node C1. Meanwhile, the measurement circuit 53 measures the current I30 at the input terminal T51A, which is coupled to the node R, to generate a measurement signal S53A representing the amount of the current I30. Then, the processing circuit 54 which is coupled to the measurement circuit 53 receives the measurement signal S53A and generates a processing signal S54 according to the measurement signal S53A. One skilled in the art knows that, for a conductor, a current following the conductor is inversely proportional to the impedance of the conductor according to Ohm's Law. Thus, the processing signal S54A derived from the current I30 through the measurement signal S53A can represent the impedance of the conductive loop 30. The memory 55 which is coupled to the processing circuit 54 receives and stores the processing signal S54A.

Figure 6B:
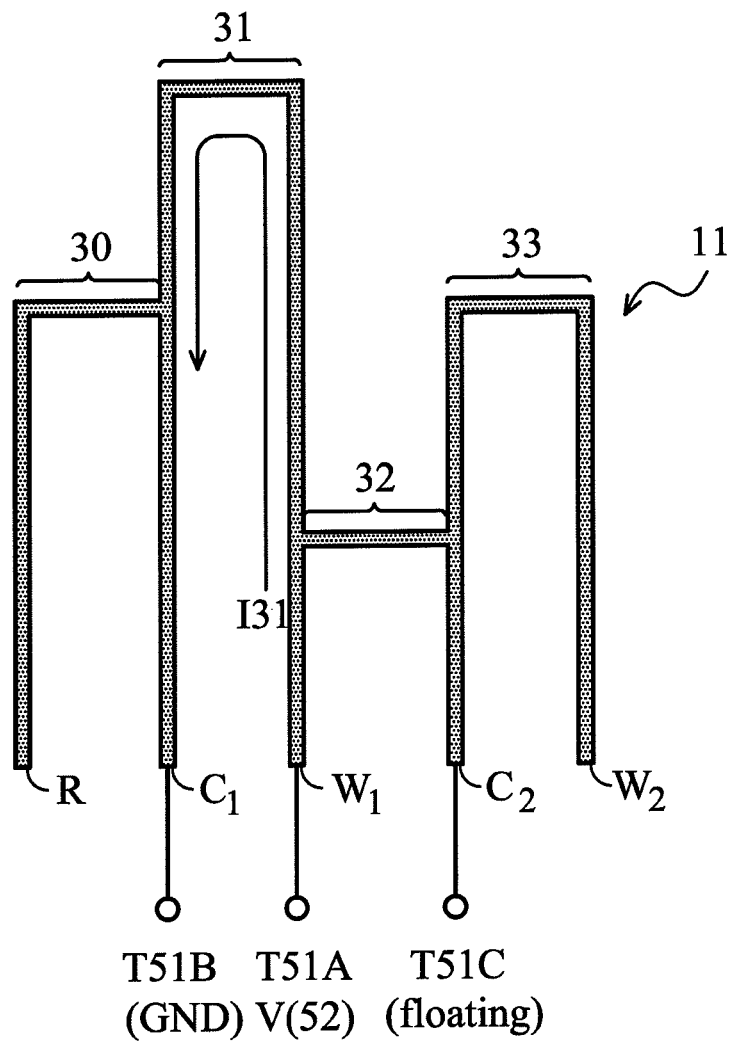

During a second measurement period, the switching circuit 51 couples the node W1 to the input terminal T51A, the node C1 to the input terminal (GND) T51B, and the node C2 to the input terminal (floating) T51C according to the control signal S50A, as shown in FIG. 6B. The generation circuit 52 generates the predetermined voltage V52 to the node W1 through the input terminal T51A according to the controls signal S50B. At this time, a current I31 is induced from the node W1 to the node C1 (GND), and the amount of the current I31 is determined according to the predetermined voltage V52 and the impedance of the conductive loop 31 formed between the node C1 and the node W1. Meanwhile, the measurement circuit 53 measures the current I31 at the input terminal T51A, which is coupled to the node W1, to generate a measurement signal S53B representing the amount of the current I31. Then, the processing circuit 54 receives the measurement signal S53B and generates a processing signal S54B according to the measurement signal S53B. According to Ohm's Law, the processing signal S54B derived from the current I31 through the measurement signal S53B can represent the impedance of the conductive loop 31. The memory 55 then receives and stores the processing signal S54B.

Figure 6C:
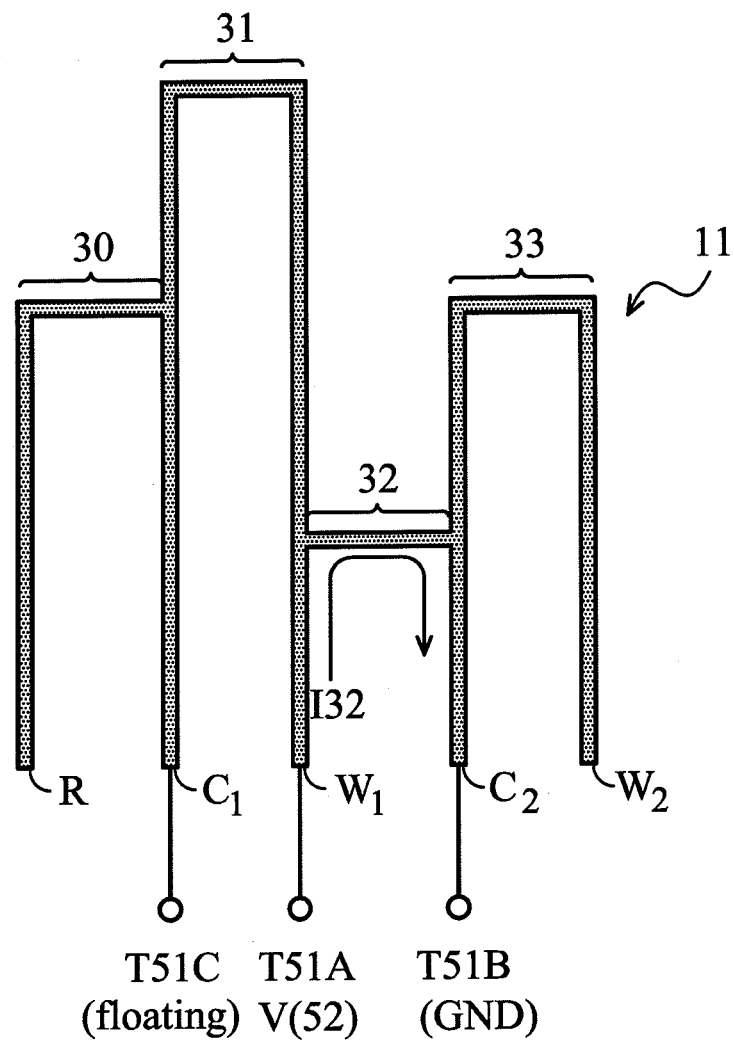

During a third measurement period, the switching circuit 51 couples the node W1 to the input terminal T51A, the node C2 to the input terminal (GND) T51B, and the node C1 to the input terminal (floating) T51C according to the control signal S50A, as shown in FIG. 6C. The generation circuit 52 generates the predetermined voltage V52 to the node W1 through the input terminal T51A according to the controls signal S50B. At this time, a current I32 is induced from the node W1 to the node C2 (GND), and the amount of the current I32 is determined according to the predetermined voltage V52 and the impedance of the conductive loop 32 formed between the node W1 and the node C2. Meanwhile, the measurement circuit 53 measures the current I32 at the input terminal T51A, which is coupled to the node W1, to generate a measurement signal S53C representing the amount of the current I32. Then, the processing circuit 54 receives the measurement signal S53C and generates a processing signal S54C according to the measurement signal S53C. According to Ohm's Law, the processing signal S54C derived from the current I32 through the measurement signal S53C can represent the impedance of the conductive loop 32. The memory 55 then receives and stores the processing signal S54C.

Figure 6D:
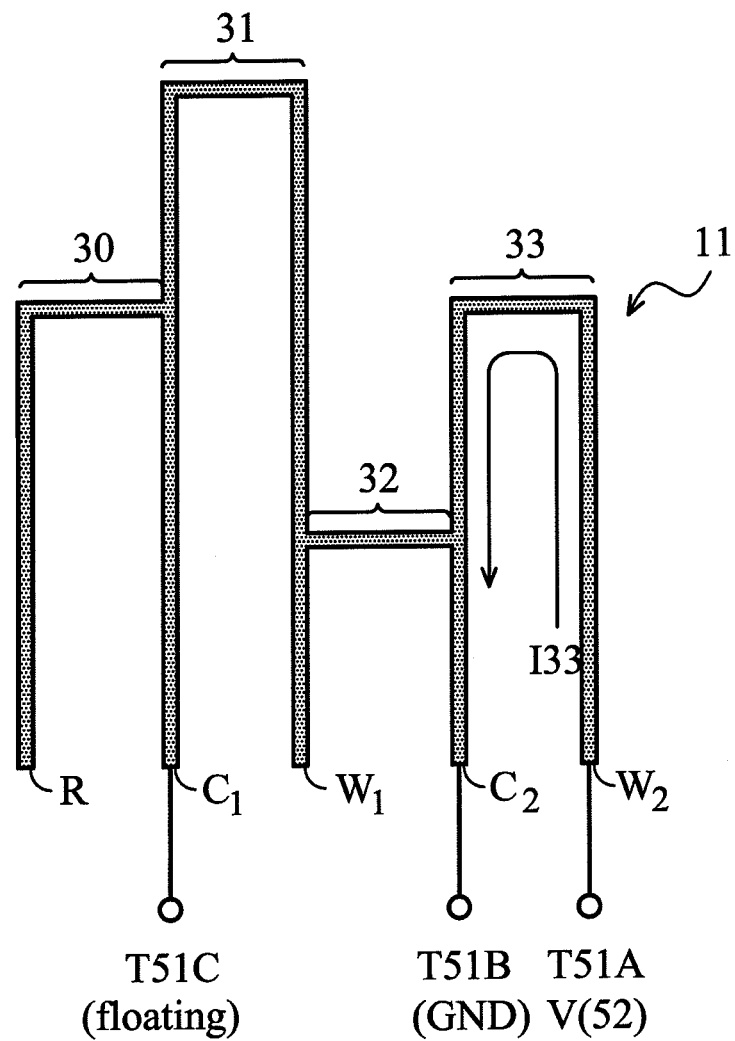

During a fourth measurement period, the switching circuit 51 couples the node W2 to the input terminal T51A, the node C2 to the input terminal (GND) T51B, and the node C1 to the input terminal (floating) T51C according to the control signal S50A, as shown in FIG. 6D. The generation circuit 52 generates the predetermined voltage V52 to the node W2 through the input terminal T51A according to the controls signal S50B. At this time, a current I33 is induced from the node W2 to the node C2 (GND), and the amount of the current I33 is determined according to the predetermined voltage V52 and the impedance of the conductive loop 33 formed between the node C2 and the node W2. Meanwhile, the measurement circuit 53 measures the current I33 at the input terminal T51A, which is coupled to the node W2, to generate a measurement signal S53D representing the amount of the current I33. Then, the processing circuit 54 receives the measurement signal S53D and generates a processing signal S54D according to the measurement signal S53D. According to Ohm's Law, the processing signal S54D derived from the current I33 through the measurement signal S53D can represent the impedance of the conductive loop 33. The memory 55 then receives and stores the processing signal S54D.

In the embodiment, the first, second, third, and fourth measurement periods occur successively. In another embodiment, the occurrence order of the first, second, third, and fourth measurements is determined by system requirements.

After all of the processing signals S54A~S54D are generated by the processing circuit 54 and received by the memory 55 for storage, the memory 55 outputs the processing signal S54A~S54D according to the control signal S50C to the comparison circuit 56. The comparison circuit 56 then performs a comparison operation to the processing signals S54A~S54D to generate comparison signals S56A~S56C according to the result of the comparison operation. For example, the comparison circuit 56 performs the comparison operation by comparing the voltage levels of the processing signals S54A~S54D. As the above describes, the processing signals S54A~S54D can represent the impedances of the conductive loops 30~33, respectively. Thus, the comparison signals S56~S56C can represent a comparison result of the impedances of the conductive loops 30~33. In the embodiment, the processing signal S54A representing the impedance of the conductive loop 30 serves as a reference signal. In other words, the impedance of the conductive loop 30 serves as a reference impedance for the comparison of the impedances of the conductive loops 30~33. In detail, the comparison circuit 56 compares the voltage level of the processing signal S54A with the voltage level of the processing signal S54B to generate the comparison signal S56A, which is the comparison result between the impedances of the conductive loops 30 and 31. The comparison circuit 56 compares the voltage level of the processing signal S54A with the voltage level of the processing signal S54C to generate the comparison signal S56B which the comparison result between the impedances of the conductive loops 30 and 32. The comparison circuit 56 compares the voltage level of the processing signal S54A with the voltage level of the processing signal S54D to generate the comparison signal S56C which the comparison result between the impedances of the conductive loops 30 and 33. For each of the comparison signals S56A~S56C, the comparison signal may have one of three different states according to the different comparison result.

After the comparison circuit 56 finishes the comparison operation to the processing signals S54A~S54D, the comparison circuit 56 transmits the comparison signals S56A~S56C to the mapping circuit 57. The mapping circuit 57 stores various values corresponding to the comparison signals S56A~S56C with various state combinations. When the mapping circuit 57 receives the comparison signals S56A~S56C, the mapping circuit 57 determines a corresponding value according to the state combination of the comparison signals S56A~S56C. The determined value serves as the value of the code of the biosensor 1 represented by the code pattern on the one side 10a of the substrate 10.

Table 1 shows corresponding relationships between the values stored in the mapping circuit 57 and the comparison signals S56A~S56C with various state combinations. In Table 1, the comparison signal with the state "M" represents that the impedance of one of the conductive loops 31~33 is equal to the impedance of the conductive loop 30 (reference impedance) according to the two compared processing signals. The comparison signal with the state "H" represents that the impedance of one of the conductive loops 31~33 is larger than the impedance of the conductive loop 30 (reference impedance) according to the two compared processing signals. The comparison signal with the state "L" represents that the impedance of one of the conductive loops 31~33 is less than the impedance of the conductive loop 30 (reference impedance) according to the two compared processing signals.

TABLE 1

| S56A | L | M | H | L | M | H | L | M | H | L | M | H | L | M |
|---|---|---|---|---|---|---|---|---|---|---|---|---|---|---|
| S56B | L | L | L | M | M | M | H | H | H | L | L | L | M | M |
| S56C | L | L | L | L | L | L | L | L | L | M | M | M | M | M |
| value | 1 | 2 | 3 | 4 | 5 | 6 | 7 | 8 | 9 | 10 | 11 | 12 | 13 | 14 |

| S56A | H | L | M | H | L | M | H | L | M | H | L | M | H |
|---|---|---|---|---|---|---|---|---|---|---|---|---|---|
| S56B | M | H | H | H | L | L | L | M | M | M | H | H | H |
| S56C | M | M | M | M | H | H | H | H | H | H | H | H | H |
| value | 15 | 16 | 17 | 18 | 19 | 20 | 21 | 22 | 23 | 24 | 25 | 26 | 27 |

For example, in the embodiment of FIGS. 3A~3B, the impedance of the conductive loop 31 is larger than the impedance of the conductive loop 30, the impedance of the conductive loop 32 is less than the impedance of the conductive loop 30, and the impedance of the conductive loop 33 is larger than the impedance of the conductive loop 30. Thus, the states of the comparison signals S56A~S56C are "H", "L", and "M", respectively. The corresponding value is 12 which serves as the value of the value of the core of the biosensor 1. Then, the bio-measurement device 40 can set at least one parameter of the measurement operation according to the code of the value "12".

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A biosensor for sensing a biological sample, having a code representing features of the biosensor, the biosensor comprising:
   a substrate; and
   a conductive layer, disposed on a first side of the substrate, wherein the conductive layer comprises:
      a first conductive loop, formed between a first node and a second node, having a first impedance; and
      a second conductive loop, formed between the second node and a third node, having a second impedance,
   wherein the code is determined according to a comparison result between the second impedance and the first impedance.

2. The biosensor as claimed in claim 1, further comprising:
   a biological reaction layer, disposed in a biological reaction area on a second side of the substrate and having a chemical reagent,
   wherein the second side is opposite to the first side, and the biological sample is disposed on the biological reaction area for contacting the chemical reagent of the biological reaction layer.

3. The biosensor as claimed in claim 2, wherein the code represents a reaction feature of the chemical reagent.

4. The biosensor as claimed in claim 3, wherein the biosensor is applied for sensing glucose of the biological sample.

5. The biosensor as claimed in claim 1, wherein, widths of the first conductive loop and the second conductive loop are substantially equal, and the first impedance and the second impedance are determined according to lengths of the first loop conductive loop and the second conductive loop, respectively.

6. The biosensor as claimed in claim 1, wherein the code represents manufacturing information of the biosensor.

7. The biosensor as claimed in claim 1, wherein the first conductive loop and the second conductive loop are disposed on the substrate by screen printing.

8. The biosensor as claimed in claim 1, wherein the biosensor is a blood glucose meter.

9. The biosensor as claimed in claim 1,
   wherein when the comparison result represents that the second impedance is larger than the first impedance, the code has a first value,
   wherein when the comparison result represents that the second impedance is equal to the first impedance, the code has a second value,
   wherein when the comparison result represents that the second impedance is less than the first impedance, the code has a third value, and
   wherein the first value, the second code, and the third value are different.

10. A bio-measurement system for sensing a biological sample, the bio-measurement system comprising:
   a biosensor having a code representing features of the biosensor, the biosensor comprising:
      a substrate, having a first side and a second side opposite to the first side;
      a biological reaction layer, disposed in a biological reaction area on the second side of the substrate and having a chemical reagent, wherein biological sample is disposed on the biological reaction area for contacting the chemical reagent of the biological reaction layer; and
      a conductive layer, disposed on the first side of the substrate, wherein the conductive layer comprises:
         a first conductive loop, formed between a first node and a second node, having a first impedance; and a second conductive loop, formed between the second node and a third node, having a second impedance; and a bio-measurement device connected to the biosensor, wherein the bio-measurement device obtains the first impedance and the second impedance and determines a value of the code according to a comparison result between the second impedance and the first impedance, and wherein the bio-measurement device performs a measurement operation to an analyte of the biological sample according to the value of the code.

11. The bio-measurement system as claimed in claim 10, wherein the code represents a reaction feature of the chemical reagent.

12. The bio-measurement system as claimed in claim 10, wherein the biosensor is applied for sensing glucose of the biological sample.

13. The bio-measurement system as claimed in claim 10, wherein, widths of the first conductive loop and the second conductive loop are substantially equal, and the first impedance and the second impedance are determined according to lengths of the first loop conductive loop and the second conductive loop, respectively.

14. The bio-measurement system as claimed in claim 10, wherein the code represents manufacturing information of the biosensor.

15. The bio-measurement system as claimed in claim 10, wherein the first conductive loop and the second conductive loop are disposed on the substrate by screen printing.

16. The bio-measurement system as claimed in claim 10, wherein the bio-measurement device comprises:
a control circuit generating a first control signal and a second control signal;
a switching circuit, coupled to the control circuit to receive the first control signal, a first input terminal, a second input terminal coupled to a reference ground, and a third input terminal with a floating state, wherein during a first measurement period, the switching circuit couples the first node to the first input terminal and the second node to the second input terminal according to the first control signal, and during a second measurement period, the switching circuit couples the third node to the first input terminal and the second node to the second input terminal the third node according to the first control signal;
a generation circuit, coupled to the control circuit to receive the second control signal, generating a predetermined voltage to the first input terminal of the switching circuit according to the second control signal;
a measurement circuit, coupled to first input terminal of the switching circuit, measuring a current at the first input terminal to generate a first measurement signal during the first measurement period and a second measurement signal during the first measurement period;
a processing circuit, coupled to the measurement circuit, receiving the first and second measurement signals, and obtaining a first and second processing signal according to the first and second measurement signals, respectively, wherein the first and second processing signal represent the first and second impedances, respectively;
a memory, coupled to the processing circuit, storing the first and second processing signals;
a comparison circuit, coupled to the memory to receive the first and second processing signals, performing a comparison operation to the first and the second processing signals to generate a comparison signal representing the comparison result;
a mapping circuit, coupled to the comparison circuit, determining the value of the code according to the comparison signal.

17. The bio-measurement system as claimed in claim 16, wherein the conductive layer further comprises:
a third conductive loop, formed between the third node and a fourth node, having a third impedance,
wherein during each of the first and second measurement periods, the switching circuit couples the fourth node to the third input terminal according to the first control signal.

18. The bio-measurement system as claimed in claim 10, wherein the bio-measurement device sets at least one parameter of the measurement operation according to the code to measure the analyte of the biological sample.

19. The bio-measurement system as claimed in claim 10, wherein the bio-measurement device comprises:
a display showing a measurement result of the measurement operation performed to the analyte.

20. The bio-measurement system as claimed in claim 10, wherein the bio-measurement system is a blood glucose measurement system.

* * * * *